(12) United States Patent
Dickinson

(10) Patent No.: US 6,675,041 B2
(45) Date of Patent: Jan. 6, 2004

(54) ELECTRONIC APPARATUS AND METHOD FOR MONITORING NET CALORIE INTAKE

(75) Inventor: Elisabeth N. Dickinson, Vancouver (CA)

(73) Assignee: Physi-cal Enterprises LP, Vancouver (CA)

(*) Notice: Subject to any disclaimer, the term of this patent is extended or adjusted under 35 U.S.C. 154(b) by 231 days.

(21) Appl. No.: 09/875,162

(22) Filed: Jun. 7, 2001

(65) Prior Publication Data
US 2002/0019585 A1 Feb. 14, 2002

Related U.S. Application Data

(63) Continuation-in-part of application No. 09/313,835, filed on May 18, 1999, now abandoned.

(51) Int. Cl.$^7$ .............................................. A61B 5/0402
(52) U.S. Cl. ........................ 600/509; 128/921; 600/300
(58) Field of Search .................................. 600/509, 520, 600/521, 523, 500–503, 300; 128/921

(56) References Cited

U.S. PATENT DOCUMENTS

| | | | |
|---|---|---|---|
| 4,159,416 A | * | 6/1979 | Brejnik et al. ................. 377/19 |
| 4,192,000 A | | 3/1980 | Lipsey |
| 4,212,079 A | | 7/1980 | Segar et al. |
| 4,312,358 A | | 1/1982 | Barney |
| 4,686,624 A | | 8/1987 | Blum et al. |
| 4,924,389 A | | 5/1990 | Gerbaulet et al. |
| 4,951,197 A | | 8/1990 | Mellinger |
| 4,966,155 A | | 10/1990 | Jackson |
| 5,033,561 A | | 7/1991 | Hettinger |
| 5,233,520 A | | 8/1993 | Kretsch et al. |
| 5,704,350 A | | 1/1998 | Williams, III |
| 5,738,104 A | | 4/1998 | Lo et al. |
| 5,795,300 A | | 8/1998 | Bryars |
| 5,807,267 A | | 9/1998 | Bryars et al. |
| 5,839,901 A | | 11/1998 | Karkanen |
| 5,853,372 A | | 12/1998 | Britton |
| 5,876,350 A | | 3/1999 | Lo et al. |
| 5,890,128 A | | 3/1999 | Diaz et al. |
| 5,941,837 A | * | 8/1999 | Amano et al. ............... 600/595 |
| 5,989,188 A | | 11/1999 | Birkhoelzer et al. |
| 6,013,009 A | | 1/2000 | Karkanen |
| 6,287,262 B1 | * | 9/2001 | Amano et al. ............... 600/500 |

FOREIGN PATENT DOCUMENTS

| | | |
|---|---|---|
| CA | 1275733 | 5/1990 |
| DE | 2949550 | 6/1981 |
| DE | 3819248 | 2/1989 |

* cited by examiner

Primary Examiner—Jeffrey R. Jastrzab
(74) Attorney, Agent, or Firm—Oyen Wiggs Green & Mutala

(57) ABSTRACT

Apparatus for tracking net consumption of calories by a user has an input to allow a user to enter the number of calories in food consumed by the user. The apparatus also includes a heart rate monitor and a timer. The heart rate monitor and timer. A processor in the apparatus can calculate the number of calories expended by the user in an exercise session from the duration of the exercise session, as measured by the timer, and the intensity of the exercise session as measured by the timer. The apparatus may be provided as a light weight wrist wearable instrument. The apparatus simplifies tracking the expenditure of calories in exercise and makes it possible to vary dietary constraints on calorie consumption in accordance with the amount of exercise in which the user has participated.

15 Claims, 6 Drawing Sheets

ELECTRONIC APPARATUS AND METHOD FOR MONITORING NET CALORIE INTAKE

RELATED APPLICATION

This application is a Continuation-in-Part to an application entitled "Electronic Apparatus and Method for Monitoring Net Calorie Intake" (U.S. patent application Ser. No. 09/313,835) filed on May 18, 1999 now abandoned.

TECHNICAL FIELD

This invention relates to apparatus and methods for tracking a person's net calorie intake over a period of time. This invention also relates to apparatus and methods for comparing a person's net calorie intake to a target net calorie consumption set by the person and warning the person when the target calorie intake is exceeded. The apparatus is provided in the form of a portable wrist-wearable instrument.

BACKGROUND

There is an increasing awareness that proper nutrition and reasonable amounts of exercise are both very important in the maintenance of good health. In affluent societies people tend to consume more food than is good for them and to exercise too little. More specifically, peoples' net calorie intake, i. e. calories consumed (typically through food) minus calories expended (typically through exercise), is too high. This contributes to weight increase. A major problem faced by people is that it can be difficult to keep track of net calorie intake, particularly where one has a diet and exercise regimen which fluctuates from day to day.

Setting and observing daily target calorie consumption levels can be useful in maintaining a healthy lifestyle. A person's target net calorie intake level varies depending on various personal characteristics, such as age and metabolism rate. It also depends on the person's weight objectives. For example, a person might set a relatively low target net calorie intake if the person wishes to lose weight. The same person might set a higher target net calorie intake if the person desires to maintain a healthy weight.

The patent literature is replete with various devices which are designed to assist a person in keeping a record of the number of calories they have consumed over a period of time. Some of these devices are described, for example, in U.S. Pat. No. 5,033,561 to Hettinger; U.S. Pat. No. 5,233,520 to Kretsh et al.; U.S. Pat. No. 4,686,624 to Blum et al.; Canadian patent No. 1,275,733; U.S. Pat. No. 4,924,389 to Ferry et al.; and U.S. Pat. No. 4,192,000 to Lipsey. A problem with such devices is that they focus solely on the calories consumed by a user. These devices do not encourage a recognition that it is the net calorie intake of a person that is important.

There are also various devices for enabling a person to track the number of calories they have expended through exercise. These include U.S. Pat. No. 5,839,901 to Karkanen; U.S. Pat. No. 4,951,197 to Mellinger; and U.S. Pat. No. 5,704,350 to Willams. Many of these devices suffer from the disadvantage that they rely upon estimates of the type and duration of exercise conducted by the user. Such estimates are often highly inaccurate and typically do not take into account the fitness level of an individual user. Typically these devices require users to tediously manually enter information about the exercises which the user has carried out. Many of these devices are unwieldy and are not practical for a user to keep handy at all times during the day.

There have been some attempts to provide devices which are capable of keeping track of both calories consumed during a given period and calories expended in the same period. For example, German patent application No's. DE3819248 and DE2949550 describe such devices. Both of these devices rely upon a user entering through a keypad information describing the types and duration of exercises which the user carries out. Only a few broad types of exercise are provided for. Neither of these devices permits reliable measurement of calories expended by a user in exercise during the day.

Segar et al. (U.S. Pat. No. 4,212,079, issued Jul. 8, 1980), discloses a calorie monitoring device which permits users to compare calories consumed with calories expended. The Segar et al. device can sound an alarm every time calories consumed exceed calories expended. Calories expended include an estimate of calories burned by an individual when "at rest" plus an estimate of calories burned by an individual when exercising. A problem with the Segar et al. device is that its estimates of energy expenditure are derived from information entered by a user regarding the types and durations of exercise. These estimates can be unreliable.

Diaz (U.S. Pat. No. 5,890,128, issued Mar. 30, 1999), discloses a handheld computer containing an extensive list of foods, with their associated caloric and fat contents. The Diaz device also includes a list of exercises, with their associated caloric values, the latter being tailored to the user's personal characteristics. A problem with this device is that its calorie expenditure calculation is imprecise.

There remains a need for apparatus which can assist users in the maintenance of healthy lifestyles by tracking both the calories consumed and the calories expended by the user and comparing it to a user defined target net calorie consumption. There is also a need for such devices which alert the user when he or she has exceeded their target net calorie consumption. This allows users to modify their behavior. There is a particular need for such devices which accurately estimate the calories expended through exercise. There is a particular need for such apparatus which is small, unobtrusive and convenient to use.

SUMMARY OF INVENTION

This invention provides a device which tracks both the number of calories consumed by a user and the number of calories expended by the user in exercise and compares the net intake level with a target net calorie consumption. The apparatus is wrist wearable and provides the user with a readily accessible indication of the net intake level with respect to the target net calorie consumption.

BRIEF DESCRIPTION OF THE DRAWINGS

In drawings which illustrate non-limiting embodiments of the invention.

DETAILED DESCRIPTION

Figure 1:
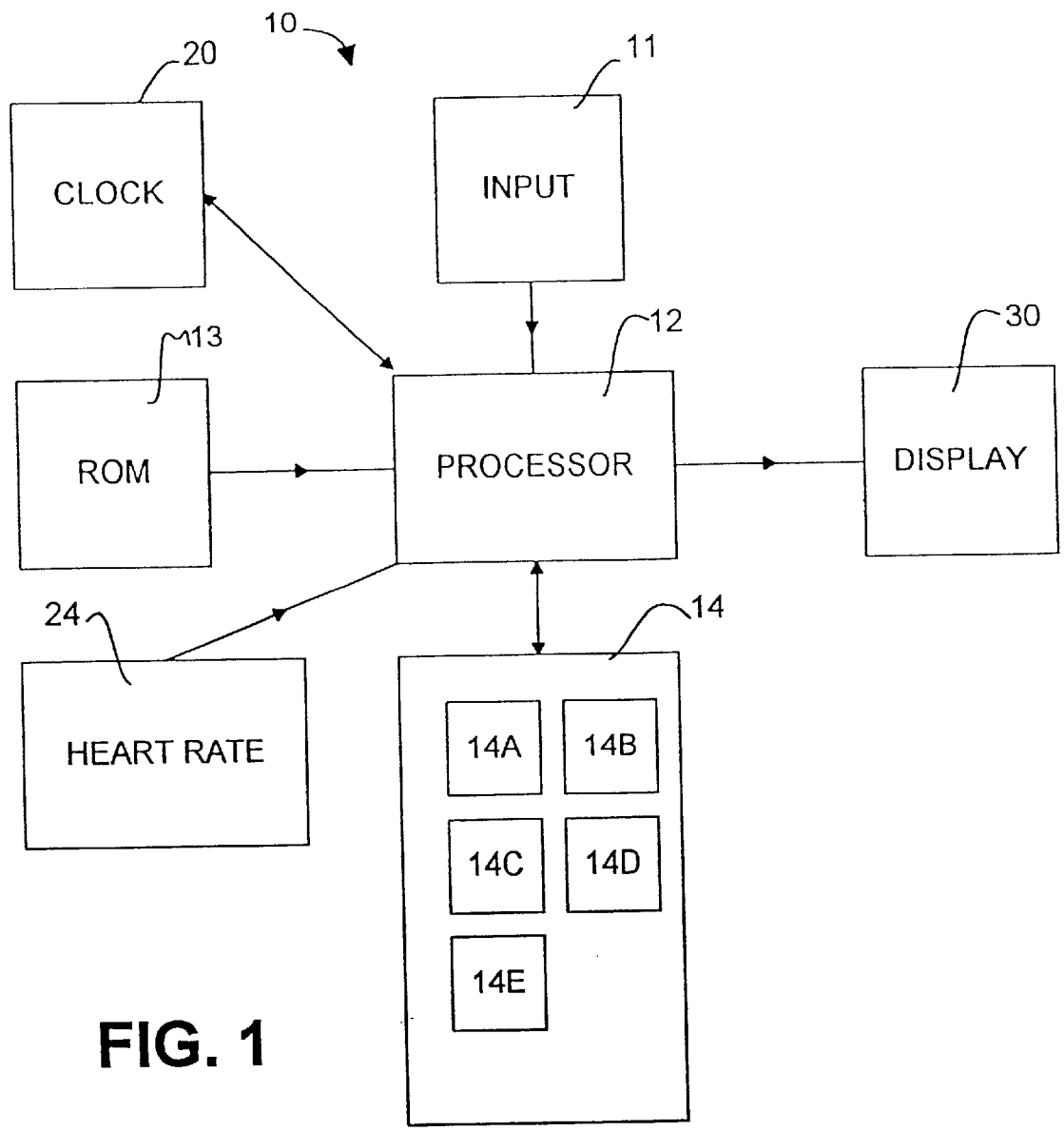
FIG. 1 is a functional block diagram of an apparatus according to the invention.
Figure 2:
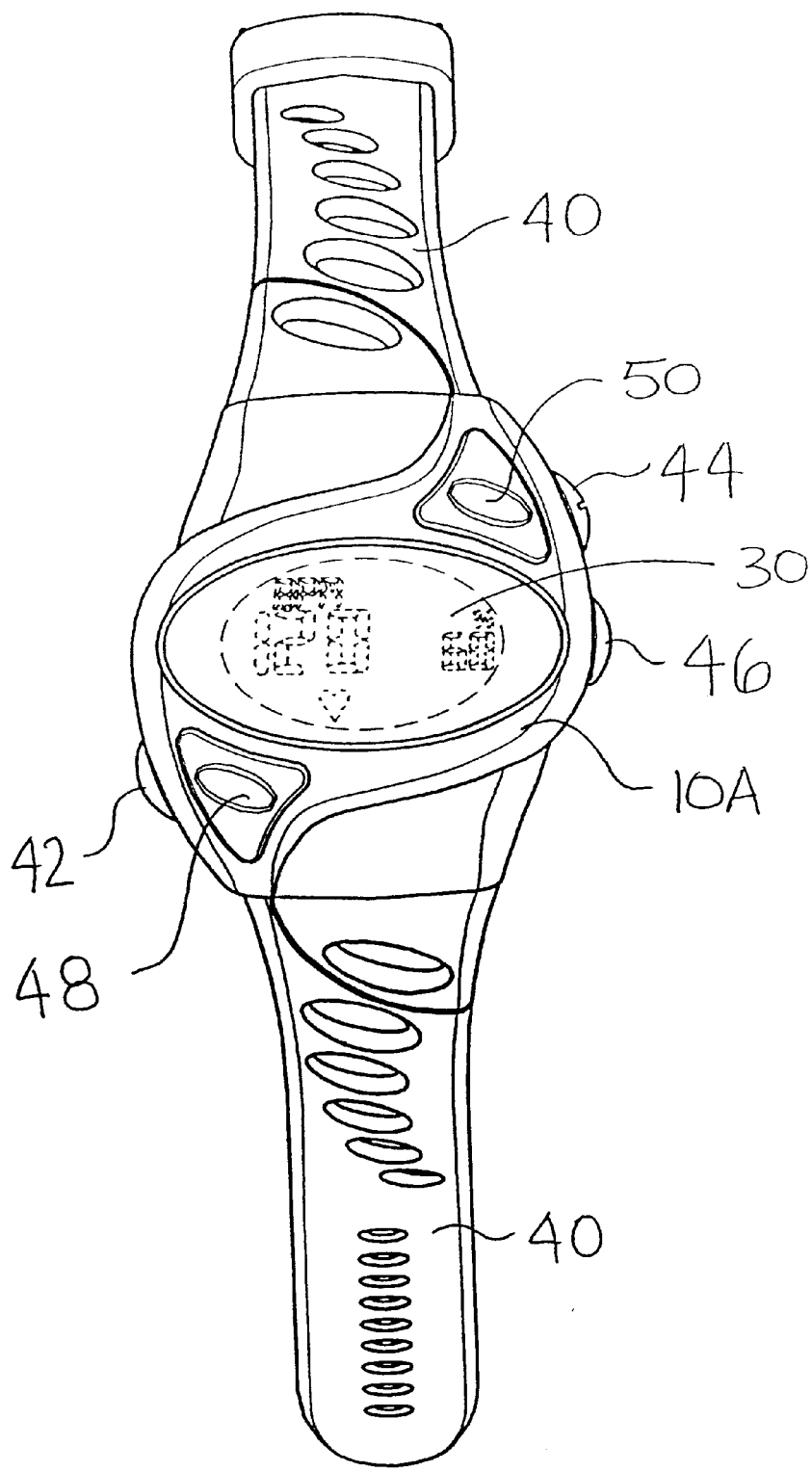
FIG. 2 is a perspective view of an apparatus according to a preferred embodiment of the invention.

FIG. 1 shows a functional block diagram of an apparatus 10 according to the invention. Apparatus 10 is provided in the form of a compact portable self contained package. Most preferably apparatus 10 is be provided in a form of a wrist-wearable instrument similar to a wrist watch. As shown in FIG. 2, apparatus 10 has a strap 40 with which apparatus 10 may be secured to a user's wrist.

Apparatus 10 has a user input 11 which allows a user to set up apparatus 10 as described below and to provide apparatus 10 with data regarding the number of calories in food consumed by the user. User input 11 may comprise a number of buttons, a keypad, a touch screen, or any other suitable, compact, means for entering information into apparatus 10.

The data entered by a user at user input 11 is provided to a processor 12 which operates as directed by a software program stored in ROM 13. Processor 12 may comprise a microprocessor. Processor 12 is preferably a type of microprocessor which is compact and has very low power consumption. For example, various microprocessors designed for use in electronic wristwatches may be used for processor 12. The model 80C51 processor made by Intel is one example of a microprocessor which may be used in an apparatus 10 according to this invention.

Processor 12 has access to a memory 14 in which it can store and retrieve data during operation. Memory 14 may have a plurality of memory locations, labelled 14A–14E in FIG. 1. As a user enters data via user input 11 regarding calories consumed, processor 12 retrieves the data from input 11, and adds this number of calories consumed to a value representing the user's net calorie intake, which is stored in a memory location 14A in memory 14.

Processor 12 can display the user's net calorie intake level (i.e. the number stored in memory location 14A) on a display 30. Display 30 may be any suitable type of graphical display. Display 30 is preferably a liquid crystal display ("LCD"). The contents of memory location 14A may be displayed continuously or, in the alternative, a user may cause processor 12 to display the contents of memory location 14A on display 30 by entering suitable commands through user input 11.

Apparatus 10 is also capable of monitoring the number of calories expended by a user through exercise. Rather than merely permitting a user to enter information about the type and duration of exercise undertaken by the user, apparatus 10 provides a timer 20 and heart rate monitor 24 which are both connected to processor 12. A user can cause processor 12 to begin timing an exercise session by entering a command through user input 11. During the exercise session, the user can periodically cause heart rate monitor 24 to measure the user's heart rate. When the user indicates that the exercise session is over, by entering a suitable command through user input 11, processor 12 computes the number of calories expended by the user during the exercise session using heart rate information provided by heart rate monitor 24. Heart rate monitor 24 is preferably of a type which detects a user's heart rate by detecting a signal between the user's wrist and a finger of the user's opposite hand. By way of example only, heart rate monitor 24 may be the type of heart rate monitor described in U.S. Pat. No. 5,738,104 entitled: EKG BASED HEART RATE MONITOR or U.S. Pat. No. 5,876,350 entitled EKG BASED HEART RATE MONITOR WITH DIGITAL FILTER AND ENHANCEMENT SIGNAL PROCESSOR, both of which are incorporated by reference herein.

The number of calories expended by a user is calculated from the user's heart rate, as measured by heart rate monitor 24 during the exercise session and from other information about the user as previously stored in a location 14B in memory 14. The stored information preferably includes the user's gender, age, and base heart rate, which is indicative of the user's general physiological condition. Processor 12 then subtracts the number of calories expended by the user from the value representing the net calorie intake which is stored in memory location 14A in memory 14. Processor 12 compares the user's net calorie intake 14A to a target amount more specifically, a target net calorie consumption (which has previously been stored in a location 14C in memory 14). So, when a user consumes calories and enters data reflecting this, the user's net calorie intake value increases. When a user expends energy by exercising, the user's net calorie intake value decreases. It will accordingly be appreciated that the net calorie intake can be less than zero.

Most preferably, processor 12 can generate a visual indicator 62 (FIG. 3) on display 30 when the user's net calorie intake approaches or exceeds the target amount stored in location 14C. Indicator 32 preferably provides a graphical indication which compares the net calorie intake 14A to the target amount 14C.

FIG. 2 is a view of an apparatus 10 according to one possible embodiment of the invention. Apparatus 10 has the overall form of a wrist watch. Apparatus 10 has a strap 40 by means of which apparatus 10 may be secured to a wearer's wrist. Apparatus 10 has a rugged body 10A which houses display 30, which is shown in greater detail in FIG. 3, and a pair of contacts 48, 50 which are associated with heart rate monitor 24. The rear face of body 10A forms a third electrical contact which contacts a user's wrist. Apparatus 10 may be largely constructed using technology which is conventional for the construction of electronic watches. Such technology is not described here in detail because it is well known to those skilled in the art. The following description describes a specific embodiment of the invention illustrated in FIG. 2 as a non-limiting example of how the invention may be practised.

Apparatus 10 of FIG. 2 has three control buttons 42, 44, and 46 which collectively constitute user input 11. Button 42 may be used to cause processor 12 to change into and out of modes in which various parameters having to do with the operation of apparatus 10, can be set. Button 44 may activate various functions including:

changing the operating mode of apparatus 10;

for selecting information in set modes as described below;

inputting information into memory 14 (or updating previously stored information); and, stopping running of timer 20.

Button 46 may be used for selecting information in set modes of apparatus 10 and may also control the operation of a lamp for the illumination of display 30.

Figure 4:
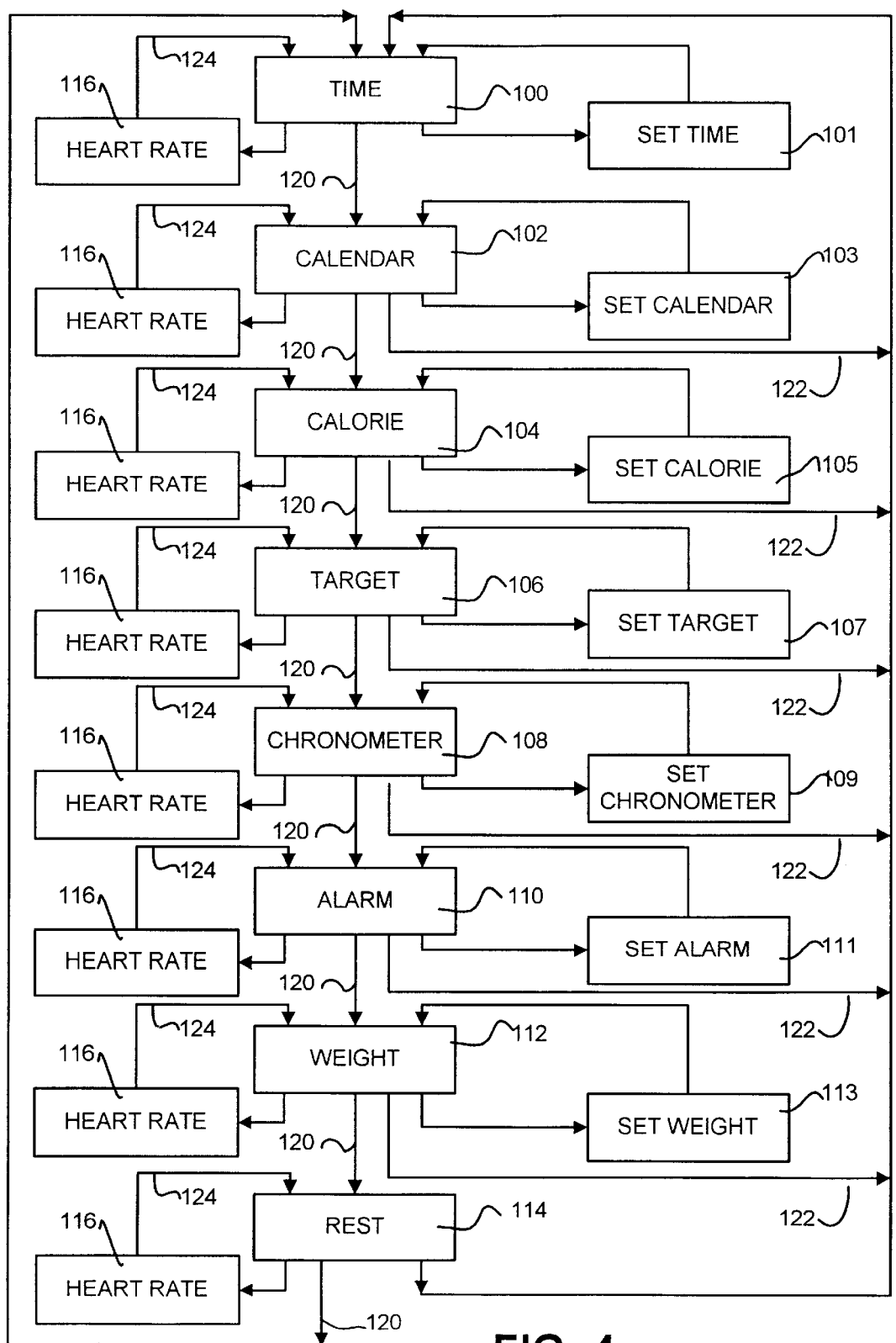
FIG. 4 is a flow chart illustrating various operational modes in apparatus according to the preferred embodiment of the invention.

FIG. 4 is a flow chart which illustrates various operating modes of apparatus 10. Apparatus 10 has a time mode 100 in which the current time is displayed on display 30, a calendar mode, 102 in which the day and date are displayed on display 30, a calorie mode 104 in which the user's net calorie intake (i.e. the total number of calories in food, including beverages, consumed by the user over a period of time less the number of calories expended by the user in exercise sessions) is displayed on display 30, a target mode 106 in which a user's target net calorie consumption is displayed on display 30, a chronometer mode 108 in which elapsed time is displayed on display 30, an alarm mode 110 in which a time at which an audible, visual or tactile alarm will be set off is displayed on display 30, a weight mode 112 in which a user's weight, as set by the user, is displayed in display 30, and a resting heart rate mode 114 in which the user's resting heart rate is displayed on display 30. A user can circulate apparatus 10 through modes 100 to 114 by repeatedly pressing button 44 as indicated by arrows 120. Time display mode 100 is the default operating mode for apparatus 10. If apparatus 10 is in any of operating modes 102 through 114 and none of buttons 42, 44 or 46 is pressed within a predetermined time interval then apparatus 10 returns to mode 100 as indicated by arrows 122.

Heart rate monitor 24 is activated whenever a user places a finger on each of contacts 48 and 50. As indicated by 116, processor 12 is programmed to display the heart rate measured by heart rate monitor 24 on display 30 for a few seconds whenever heart rate monitor 24 completes the measurement of a user's heart rate. A user can thereby measure his or her heart rate at any time. If heart rate monitor 24 fails to detect a user's heart rate then, after a few seconds, apparatus 10 returns to the operating mode it was in before the user activated heart rate monitor 24 as indicated by arrows 124.

Each of operating modes 100 through 112 have a corresponding set mode. For example modes 100 and 102 have corresponding set modes 101 and 103 which allow a user to respectively set the current time and current date by manipulating buttons 42, 44 and 46. Such functions are conventional in electronic watches and will not be described here further.

Prior to using apparatus 10 for the first time, a user provides certain information to apparatus 10 through input 11. This information preferably includes the user's sex, birth date (from which the user's age can be calculated), resting heart rate (as measured by heart rate monitor 24), weight and target net calorie consumption.

When apparatus 10 is in calorie mode 104, a user can use calorie set mode 105 to enter into apparatus 10 the number of calories in the food which the user has consumed. For example, if a user eats a bran muffin containing 150 calories then the user would place apparatus 10 into mode 104 by pressing button 44 twice and would then enter calorie setting mode 105 by pressing and holding button 42 for a short time, such as 2 seconds.

Once apparatus 10 is in calorie setting mode 105, the user can enter the number of calories consumed, in this case 150, by using buttons 42, 44 and 46 to set values for individual digits in the number of calories consumed. For example, a user may use button 42 to select, in turn, individual digits in a number on display 30. For each digit, the user can use buttons 44 and 46 to respectively increment or decrement the displayed value so as to set the desired value. After the user has set the appropriate number of calories, then the user can cause processor 12 to add the set number of calories to the user's net calorie intake as recorded in memory location 14A by holding down button 44 for predetermined time. The user can thus keep in memory location 14A a value indicating the user's net calorie intake during the course of the day, or some other period of time.

Apparatus 10 permits the net calorie intake number stored in memory location 14A to be reset to zero. This may be done manually by a user who enters a suitable command via input 11. In use the user's net calorie intake number will be reset at the start of each day (or another suitable period). Apparatus 10 could automatically reset the net calorie intake number to zero at a specific time, such as 3 a.m., in addition to or instead of, allowing a user to manually reset the number.

A user can set a target number of for the net calorie consumption by causing apparatus 10 to enter target setting mode 107 from target mode 106 by pressing and holding button 42 for a short interval. Once apparatus 10 is in target setting mode 107 then the user can set a target number in essentially the same manner described above in respect of calorie set mode 105.

Figure 5:
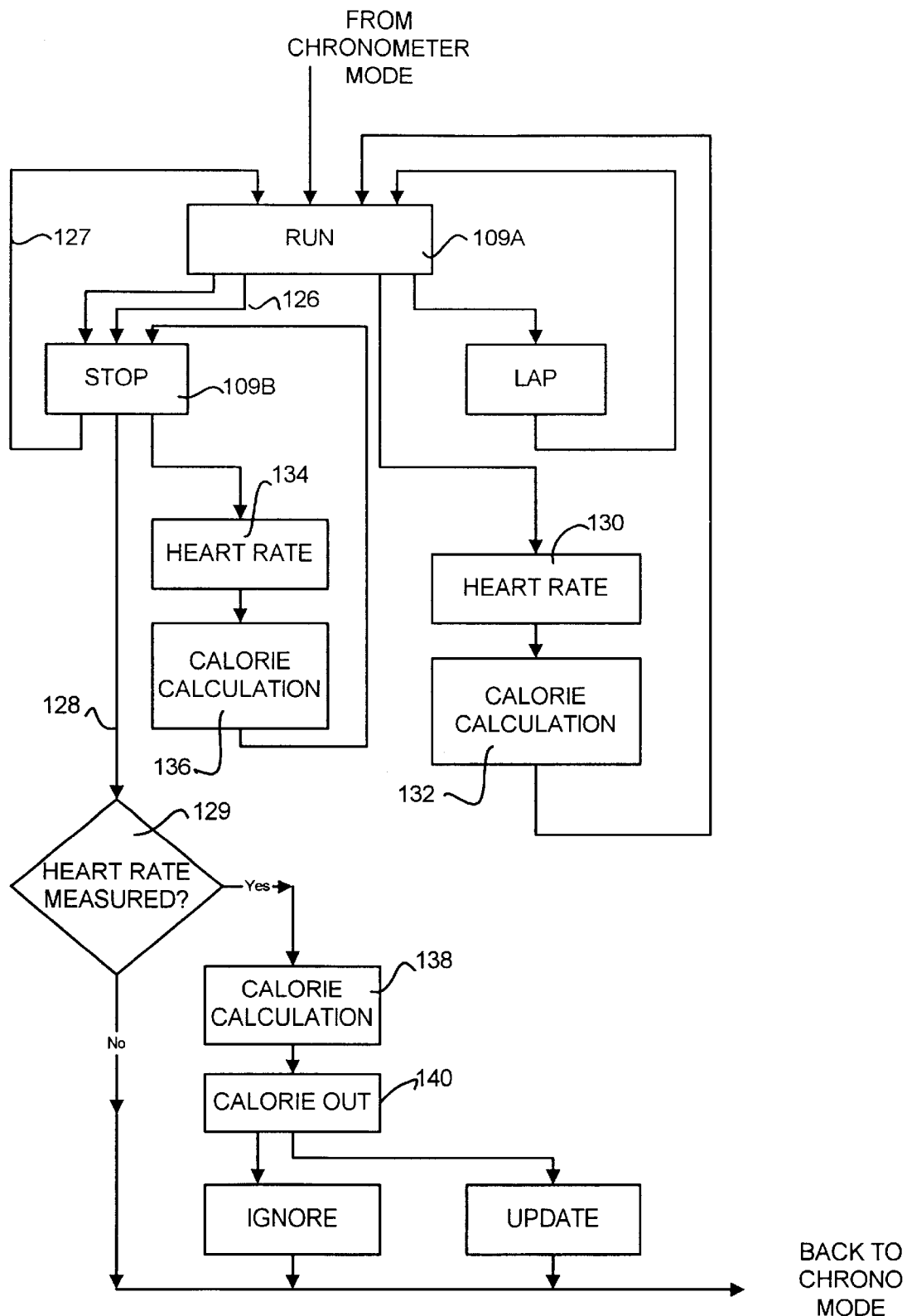
FIG. 5 is a flow chart illustrating modes and steps in computing calories expended during exercise sessions; and, FIG. 6 is a flow chart illustrating a method of weight monitoring and control according to the preferred embodiment of the invention.

To measure a number of calories expended by a user during exercise, the user places apparatus 10 in chronometer mode 108 as described above, and causes apparatus 10 to enter chronometer setting mode or exercise mode 109 by pressing button 42 for a short period of time. Once apparatus 10 has entered exercise mode 109, pressing button 42 causes timer 20 to start measuring elapsed time. As shown in FIG. 5, when apparatus 10 is in exercise mode 109 with timer 20 running as indicated by 109A, the user may periodically cause apparatus 10 to measure his or her heart rate as indicated at 130 by placing fingers on contacts 48 and 50. Each time this is done, apparatus 10 computes the number of calories expended by the user since the beginning of the exercise session as indicated at 132 and displays the result on display 30. Thus, the user can obtain ongoing feedback regarding the effectiveness of the current exercise session in expending calories. This tends to reinforce the user's resolve to carry on with the exercise session.

While in exercise mode 109A timer 20 may be stopped by pressing button 44 as indicated by arrow 126, thereby placing apparatus 10 in mode 109B. From mode 109B the user may cause apparatus 10 to measure his or her heart rate and compute and display a number of calories expended during the exercise session, as described above, and as indicated by 134 and 136. From mode 109B the user can cause apparatus 10 to return to mode 109A by pressing button 42 as indicated by arrow 127. In the alternative, the user can press button 44 to cause apparatus 10 to compute a number representing a total number of calories expended by the user during the exercise session as indicated by arrow 128. Apparatus 10 first checks to make sure that a heart rate has been measured (step 129). If no heart rate was measured, processor 12 causes apparatus 10 to return to mode 108 without updating the user's net calorie intake number recorded in location 14A. The total number of calories is computed in step 138 and displayed in step 140. The user can then press and hold button 44 for a predetermined amount of time to instruct processor 12 to update the contents of memory 14 by subtracting the number computed in step 138 from the value in memory location 14A. In the alternative, the user can press button 42 to return apparatus 10 to mode 108 without updating the net number of calories recorded in location 14A.

Processor 12 compares the net calorie intake of the user to the target stored in memory location 14C and displays a visual indicator on display 30 to indicate the relationship between the target 14C and the cumulative net calorie intake 14A. Preferably the visual indicator displays the magnitude of the net calorie intake relative to target 14C.

Figure 3:
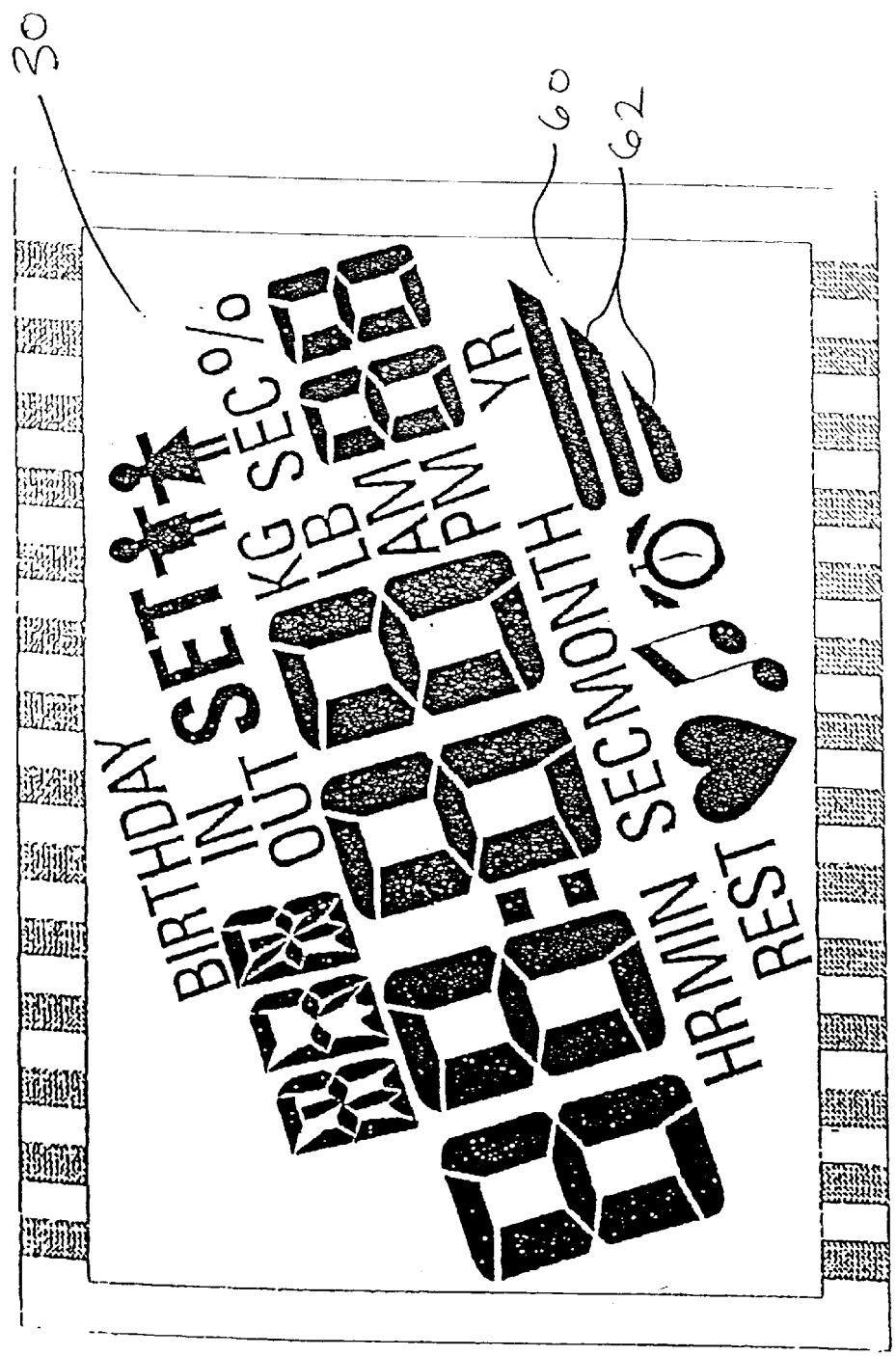
FIG. 3 is a plan view illustrating segments in a display according to the preferred embodiment of the invention.

For example, display 30 may include a bar graph 60 having a number of segments 62 (FIG. 3). In the illustrated embodiment bar graph 60 has three segments. The first segment 62A may be turned on when the net calorie intake 14A exceeds one third of the target 14C but is less than two thirds of the target 14C. The first and second segments 62A and 62B of bar graph 60 may both be turned on if the net calorie intake 14A exceeds two thirds of target 14C but is less than target 14C. All three segments 62 of bar graph 60 may be turned on if the net calorie intake 14A has reached or exceeded target 14C.

Apparatus 10 may sound an audible alarm when it first detects that the net calorie intake 14A has reached or exceeded target 14C. In a preferred embodiment, apparatus 10 sounds an audible alarm whenever a user enters a number of calories in food to be consumed by the user and thereby causes the net calorie intake 14A to reach or exceed target 14C.

Apparatus 10, as described above, encourages a balanced dietary and exercise regime. The user sees the net number of calories displayed on display 30 as opposed to a total number of calories. The user can keep net calorie intake to within a target range by exercising more. If the user has had a lot of exercise in one day then the user can eat more without being distracted or distressed by seeing displayed a larger-than-usual number of calories consumed. If the user trains himself or herself to enter calories in food to be consumed before actually eating the food, then the use of apparatus 10 promotes planning food consumption in advance. The use of apparatus 10 can also promote sensible eating since a user can be warned in advance if eating certain food would cause the user to exceed his or her target net calorie consumption 14C.

The calories expended by a user during exercise may be calculated by various formulae. The following formula has been found to produce satisfactory results:

$$C_{EXP} = \frac{T \times (MET \times 3.5 \times W)}{200} \quad (1)$$

Where: $C_{EXP}$ is the number of calories expended by the user in the exercise session; T is the duration of the exercise session in minutes as measured by timer 20; W is the user's weight in kilograms as recorded in memory location 14B; and MET is a factor which is calculated for the user according to the user's sex as recorded in memory location 14B, resting heart rate as measured in mode 114 and stored in memory location 14B, maximum heart rate as calculated from the user's age as stored in memory location 14B, and last measured current heart rate as measured in mode 109. For a male with a rest heart rate of less than 60 beats per minute, MET may be given by the following formula:

$$MET = 1 + \frac{CHR - RHR}{MHR - RHR} \times 11 \quad (2)$$

Where CHR is the user's current heart rate as last measured during the exercise session, RHR is the user's resting heart rate; and, MHR is the user's maximum heart rate. MHR may be calculated from the user's age in years as follows for a male user:

$$MHR = 214 - 0.8 \times AGE \quad (3)$$

where AGE is the user's age in years. MHR may be calculated from the user's age as follows for a female user:

$$MHR = 209 - 0.7 \times AGE \quad (4)$$

For a male user with a rest heart rate of greater than 60 beats per minute or a female user with a rest heart rate of less than 60 minutes MAT may be given as follows:

$$MET = 1 + \frac{CHR - RHR}{MHR - RHR} \times 9 \quad (5)$$

Finally, for a female with a rest heart rate of greater than 60 beats per minutes MET may be given by a formula as follows:

$$MET = 1 + \frac{CHR - RHR}{MHR - RHR} \times 7 \quad (6)$$

It can be appreciated that an apparatus 10 according to the invention has several advantages. The apparatus encourages users to exercise and adjusts dietary restrictions, on the number of calories to be consumed by a user, to take into account the user's exercise level. The apparatus greatly simplifies the task of tracking the expenditure of calories in exercise and is more accurate than previous methods which require users to guess at the duration and intensity of exercise sessions. Further, in computing the number of calories expended in exercise, apparatus 10 can take into account the user's age, gender and actual physiological condition.

Figure 6:
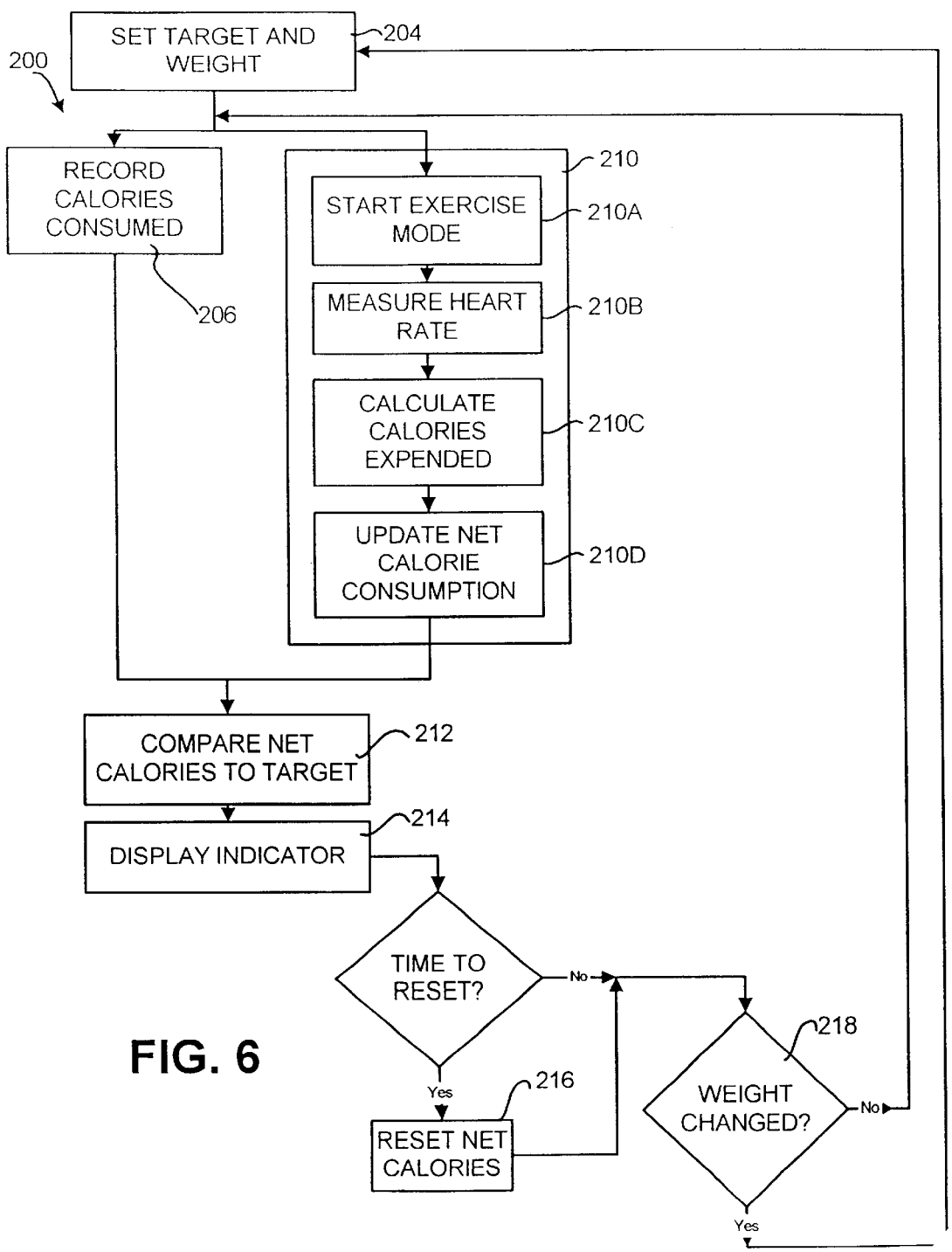

The inventor considers that two important elements in any successful program of weight reduction and control are planning and recording meals and exercise sessions. A user may use apparatus 10 to assist in planning and recording meals and exercise sessions in a method for weight control according to the invention. In method 200, which is shown in FIG. 6, a user first enters initial information about the user's weight, gender etc. into apparatus 10, determines a target net calorie consumption and records the calorie target in apparatus 10 as described above (step 204). If the user desires to lose weight then the calorie intake target is preferably about 500 to 1000 calories less than the number of calories that a user would need to consume to maintain the user's current weight. If the user desires to gain weight then the user can set a target net calorie consumption which is greater than the number of calories that the user would need to consume to maintain his or her current weight.

The target net calorie consumption may be set, for example, by determining an approximation of the user's resting metabolic rate RMR, adding to the RMR a number approximating the number of extra calories the user expends through daily activity and subtracting 500 to 1000 calories from the result. An approximation of a user's RMR may be obtained by multiplying the user's weight, measured in pounds, by 10. An approximation of the number of calories used in daily activities may be obtained by multiplying the RMR by a factor determined by the activity level of the user's lifestyle. If the user leads a sedentary lifestyle (e.g. the user sits most of the day at work and at home and drives or rides in a car to get around) the factor is in the range of about 20% to 40%. If the user leads a moderate lifestyle (e.g. the user is more active at work and at home, rides to work, uses stairs, does housework) then the factor is in the range of about 40% to 60%. If the user leads an active lifestyle (e.g. the user is very physically active at work and at home, and performs strenuous physical labour such as construction work) then the factor is in the range of about 60% to about 80%. Calculating a target net calorie consumption is not an exact science but is preferred because it is a more efficient way to focus a user's attention on the true indicators of weight reduction (or increase, or maintenance depending on the circumstances). The target net calorie consumption may be calculated using other formulae which are known to, or may be readily devised by those skilled in the art.

The user then proceeds to eat meals and to record the number of calories, contained in the meals, in apparatus 10 as described above (step 206). This causes apparatus 10 to add the number of calories consumed to the user's net calorie intake 14A. The user also exercises (step 210). At the beginning of the exercise session the user places apparatus 10 into exercise mode 109 (step 210A). During exercise, the user uses apparatus 10 to monitor his or her heart rate (step 210B), and, at the end of the exercise session, the user allows apparatus 10 to compute a number of calories expended during the exercise session, (step 210C). The user can then cause apparatus 10 to subtract the number of calories expended by the user from the user's net calorie intake (step 210D).

Apparatus 10 periodically compares (step 212) a user's net calorie intake to the target net calorie consumption and displays a visible or audible indication telling the user when the target has been reached (step 214). In the preferred embodiment, the comparison is made after each time the user has inputted data regarding either calorie consumption, either calorie expenditure. After the end of each day (or other period) the user resets the net calorie intake stored in apparatus 10 (step 216).

The user periodically weighs himself or herself to see whether his or her weight has changed (step 218). As the user's weight changes, the user periodically recalculates the user's target net calorie consumption and stores the result, and the user's weight in apparatus 10.

Through the use of method 200 in conjunction with apparatus 10 the user's mind is focussed on the user's dietary intake as well as on the user's exercise. These factors can help the user to achieve a healthier lifestyle.

As will be apparent to those skilled in the art in the light of the foregoing disclosure, many alterations and modifications are possible in the practice of this invention without departing from the spirit or scope thereof. For example:

heart rate monitor 24 has been described as being of a type which requires a user to place a finger on each of sensors 48 and 50 in order to measure a user's heart rate. This is preferable. Other types of heart rate monitoring technology could possibly also be used in the invention. It is necessary that heart rate monitor 24 be capable of sensing a user's heart rate at rest and during exercise and that heart rate monitor 24 be sufficiently compact and sufficiently low in power consumption for use in an apparatus 10 according to the invention.

While specific formulae have been provided above for the calculation of calorie consumption during exercise, a user's maximum heart rate and target net calorie consumption, other formulae which provide similar results could also be used.

While the invention has described the computation of calories expended during an exercise session on the basis of the last heart rate measurement made during the exercise session the invention could compute calories expended on the basis of two or more different heart rate measurements made during the exercise session. This could be done, for example, by each time a heart rate measurement is made, calculating the calorie expenditure since the last heart rate measurement and adding the result to a running total. When multiple heart rate measurements are used to calculate calories expended during exercise the results can be more accurate than when only a single heart rate measurement is used. In most exercise sessions the user's heart rate and energy output will fluctuate significantly over the course of the exercise session.

In the further alternative, a heart rate measurement other than the last heart rate measurement could be used to compute the calories expended during an exercise session. By way of example only, the highest measured heart rate could be used, the median of a plurality of measured heart rates could be used, or the average of the highest and lowest of two or more measured heart rates could be used to compute the calories expended in an exercise session.

As an alternative to keeping a single value representing a user's "net" calorie intake, apparatus 10 could separately track total calories consumed by the user and total calories expended by the user during exercise. The user's net calorie intake could then be calculated by subtracting the number of calories expended by the user in various exercise sessions (as stored by processor 12 in memory 14) from the number of calories in food consumed by the user (as stored by processor 12 in memory 14). The calculated net calorie intake can then be stored in memory location 14A and used as described above. In the further alternative, a single memory location 14A may be used to track net calorie intake, as described above, and apparatus 10 could keep separate track of calories in food consumed by a user and/or calories expended by the user in exercise.

The various functional aspects of apparatus 10 do not need to be provided by discrete components. Aspects such as processor 12, ROM 13 and memory 14 may be, and typically will be, incorporated into a single chip.

The ornamental appearances of the apparatus 10 as shown in FIG. 2 and display 30 as shown in FIG. 3 are included for the purpose of example but are not required for the practice of this invention. These ornamental aspects are proprietary to the owner of this invention.

While the above specification describes tracking and displaying numbers of calories in food consumed by a user and numbers of calories expended during exercise, the units in which the caloric content of the food consumed by the user or the energy expended by the user are expressed are not important to the invention. The apparatus may, for example, display net calorie intake as "points" and receive as input a number of points which represents the caloric content of food eaten (or to be eaten) by the user.

Accordingly, the scope of the invention is to be construed in accordance with the substance defined by the following claims.

What is claimed is:

1. A wrist wearable apparatus for comparing the net calorie intake of a user over a period of time, with a user defined target net calorie consumption, the apparatus comprising:
   (a) a housing;
   (b) a strap attached to the housing for attaching the housing to a user's wrist;
   (c) a user input on the housing;
   (d) a processor in the housing and connected to receive information from the user inputs;
   (e) a memory in the housing and accessible to the processor, the memory comprising:
      (i) a memory location for storing a calculated net calorie intake value; and,
      (ii) a memory location for storing a target net calorie consumption value representing a preferred net calorie consumption value for the user;
   (f) a heart rate monitor connected to the processor;
   (g) a timer in the housing connected to the processor; and,
   (h) a display on the housing, the display comprising an indicator and connected to the processor,
wherein the processor is adapted to compute and display on the display a calculated net calorie intake value based upon:

data entered by a user through the user input regarding the number of calories consumed by the user during a period of time; and a number of calories determined by the processor from data obtained by the processor from the timer and the heart rate monitor to have been expended by the user in exercise during the period of time wherein, when the apparatus is in an exercise mode, the processor executes instructions which cause it to cause the timer to start measuring an elapsed time in response to an input at the user input and, while the time is measuring the elapsed time, to compute from heart rate measurements made by the heart rate monitor, and display on the display, a number of calories expended by the user since the beginning of the elapsed time; and, wherein the processor calculates the number of calories expended by a user during an exercise session using the formula:

$$C_{EXP} = \frac{T \times (MET \times 3.5 \times W)}{200}$$

or a mathematical equivalent thereof where: $C_{EXP}$, is the number of calories expended by the user in the exercise session; T is the duration of the exercise session as measured by the timer; W is the user's weight in kilograms as recorded in the memory; and MET is a factor which is calculated for the user according to the user's gender, resting heart rate, age and measured heart rate.

2. The apparatus of claim 1 wherein the heart rate monitor comprises at least one contact exposed on a front face of the housing and a contact exposed on a rear face of the housing and the heart rate monitor measures a user's heart rate by monitoring electrical signals between the exposed contacts.

3. The apparatus of claim 2 wherein the heart rate monitor comprises two contacts exposed on the front face of the housing and the heart rate monitor is operative to measure a user's heart rate when a user places two fingers on the two contacts exposed on the front face of the housing while the contact on the rear face of the housing is in contact with the user's wrist.

4. The apparatus of claim 1 wherein the apparatus comprises a location in the memory which stores a resting heart rate measured by the heart rate monitor and the processor is adapted to compute a number of calories expended by a user during an exercise session based on the resting heart rate and a measured heart rate as measured by the rate monitor.

5. The apparatus of claim 4 wherein the apparatus comprises a location in the memory which stores data indicating a user's gender in the memory and the processor is adapted to compute a number of calories expended by the user during an exercise session based upon the resting heart rate, the measured heart rate and the gender.

6. A wrist wearable apparatus for comparing the net calorie intake of a user over a period of time, with a user-defined target net calorie consumption, the apparatus comprising:

a housing;

a strap attached to the housing for attaching the housing to a user's wrist;

a user input on the housing;

a processor in the housing and connected to receive information from the user inputs;

a memory in the housing and accessible to the processor, the memory comprising:

(i) a memory location for storing a calculated net calorie intake value; and, (ii) a memory location for storing a target net calorie consumption value representing a preferred net calorie consumption value, for the user;

a heart rate monitor connected to the processor;

a timer in the housing connected to the processor; and, a display on the housing, the display comprising an indicator and connected to the processor, wherein the processor is adapted to compute and display on the display a calculated net calorie intake value based upon:

data entered by a user through the user input regarding the number of calories consumed by the user during a period of time; and a number of calories determined by processor from data obtained by the processor from the timer and the heart rate monitor to have been expended by the user in exercise during the period of time;

wherein the heart rate monitor comprises two contacts exposed on a front face of the housing and a contact exposed on a rear face of the housing and the heart rate monitor measures a user's heart rate by monitoring electrical signals between the exposed contacts and the heart rate monitor is operative to measure a user's heart rate when a user places two fingers on the two contacts exposed on the front face of the housing while the contact on the rear face of the housing is in contact with the user's wrist;

wherein, when the apparatus is in an exercise mode, the processor executes instructions which cause it to cause the timer to start measuring an elapsed time in response to an input at the user input and, while the time is measuring the elapsed time, to compute from heart rate measurements made by the heart rate monitor, and display on the display, a number of calories expended by the user since the beginning of the elapsed time wherein the apparatus comprises a location in the memory which stores a resting heart rate measured by the heart rate monitor, a location in the memory which stores data indicating a user's gender in the memory and a location in the memory which stores data indicating a user's ace in the memory and the processor is adapted to compute a number of calories expended by the user during an exercise session based upon the resting heart rate, the measured heart rate, the gender, and the age; and, wherein the processor calculates the number of calories expended by a user during an exercise session using the formula:

$$C_{EXP} = \frac{T \times (MET \times 3.5 \times W)}{200}$$

or a mathematical equivalent thereof where: $C_{EXP}$ is the number of calories expended by the user in the exercise session; T is the duration of the exercise session as measured by the timer; W is the user's weight in kilograms as recorded in the memory; and MET is a factor which is calculated for the user according to the user's gender, resting heart rate, age and measured heart rate.

7. The apparatus of claim 6 wherein the processor is adapted to compare regularly the net calorie intake value with the target net calorie consumption value and indicate, via the indicator, a relative magnitude of the net calorie intake and the target net calorie consumption.

8. The apparatus of claim 7 wherein the indicator comprises a multi-segmented bar graph.

9. The apparatus of claim 8 wherein the bar graph comprises first, second and third segments and the processor executes instructions which cause it to:
- turn on the first segment when the net calorie intake exceeds one third of the target but is less than two thirds of the target;
- turn on both the first and second segments when the net calorie intake exceeds two thirds of the target but is less than the target; and,
- turn on all of the first, second and third segments when the net calorie intake equals or exceeds the target.

10. The apparatus of claim 9 comprising an audible alarm activated by the processor whenever adding calories in food consumed by the user to the calculated net calorie intake value would cause the calculated net calorie intake value to exceed the target net calorie consumption value.

11. The apparatus of claim 10 wherein the user input comprises first, second and third buttons on the housing and, when the apparatus is in a calorie set mode, the processor displays a number representing a number of calories consumed by a user, the number comprising a plurality of digits, in response to activation of the first button, the processor selects one of the digits, in response to activation of the second button the processor increments the selected digit, and, in response to activation of the third button the processor decrements the selected digit.

12. Wrist wearable apparatus for monitoring a net calorie intake of a user, the apparatus comprising:
(a) a housing;
(b) a strap on the housing for attaching the housing to a user's wrist;
(c) a data store in the housing for holding net calorie intake information for a user;
(d) an input on the housing for receiving calorie intake information entered by a user;
(e) a heart rate monitor in the housing; and,
(f) a processor in the housing, the processor running software instructions which cause the processor to:
- increase a value in the store by an amount indicated by the calorie intake information upon receiving the calorie intake information at the input;
- receive heart rate information for a user from the heart rate monitor, compute calorie expenditure information therefrom and automatically reduce the value in the store by an amount indicated by the calorie expenditure information wherein the calorie expenditure information comprises a number of calories expended by a user during an exercise session and the processor calculates the number of calories expended by a user during an exercise session using the formula:

$$C_{EXP} = \frac{T \times (MET \times 3.5 \times W)}{200}$$

or a mathematical equivalent thereof where: $c_{EXP}$ is the number of calories expended by the user in the exercise session; T is the duration of the exercise session as measured by the timer; W is the user's weight in kilograms as recorded in the memory; and MET is a factor which is calculated for the user according to the user's gender, resting heart rate, age and measured heart rate.

13. A method for comparing the net calorie intake of a person during a period of time with a user defined target net calorie consumption, a method comprising:

(a) providing apparatus having a user input, a heart rate monitor, a timer, a processor, a memory and a display;
(b) periodically entering via the user input first data representing a first number of calories in food consumed by the person and allowing the processor to automatically add the first number to a value in a memory location in the memory;
(c) for each of one or more exercise sessions:
- timing the exercise session with the timer;
- measuring a heart rate of the person with the heart rate monitor;
- in the processor, in response to measuring the heart rate, computing a second number representing calories expended by the person in the exercise session and subtracting the second number from the value in the memory location; and,
(d) comparing the contents of the memory location to the target value stored in the memory and indicating on the display relative magnitudes of the net calorie intake and target net calorie consumption wherein computing the second number comprises calculating the number of calories expended by a user during an exercise session using the formula:

$$C_{EXP} = \frac{T \times (MET \times 3.5 \times W)}{200}$$

or a mathematical equivalent thereof where: $C_{EXP}$ is the number of calories expended by the user in the exercise session; T is the duration of the exercise session as measured by the timer; W is the user's weight in kilograms as recorded in the memory; and MET is a factor which is calculated for the user according to the user's gender, resting heart rate, age and measured heart rate.

14. The method of claim 13 comprising displaying the contents of the memory location on a display.

15. A method for weight control, the method comprising:
(a) providing a portable wrist wearable apparatus capable of:
(i) storing a target net calorie consumption value for a time period and a user's weight;
(ii) recording a number of calories in food consumed by a user;
(iii) timing a user's exercise sessions;
(iv) monitoring a user's heart rate during the exercise sessions;
(v) automatically computing calories expended by the user in the exercise sessions using durations of the exercise sessions and the user's heart rate and weight;
(vi) calculating a net calorie intake number by the user; and
(vii) comparing the net calorie intake number to the stored target net calorie consumption value,
(b) storing a user's weight and target net calorie consumption value in the apparatus;
(c) during a first time period monitoring the user's net calorie consumption value by:
(i) recording in the apparatus a number of calories in food consumed by the user;
(ii) while the user exercises, using the apparatus to time an exercise session, measure the user's heart rate during the exercise session and compute a number of calories expended by the user in the exercise session;
(iii) in the apparatus comparing the user's net calorie intake number to the target net calorie consumption value; and (iv) displaying on the apparatus an indicator which shows the user when the user's net calorie intake number has reached the target net calorie consumption value, (d) after the end of the time period resetting the net calorie intake number to zero; and (e) repeating steps (c) to (d) for subsequent time periods wherein using the apparatus to compute the number of calories expended by the user in the exercise session comprises operating the processor to compute a result of the formula:

$$C_{EXP} = \frac{T \times (MET \times 3.5 \times W)}{200}$$

or a mathematical equivalent thereof where: $C_{EXP}$ is the number of calories expended by the user in the exercise session; T is the duration of the exercise session as by the timer: W is the user's weight in kilograms as recorded in the memory; and MET is a factor which is calculated for the user according to the user's gender, resting heart rate, age and measured heart rate.

* * * * *